United States Patent [19]

Burns et al.

[11] Patent Number: 4,552,958
[45] Date of Patent: Nov. 12, 1985

[54] METHOD OF SEPARATING PRIMARY AMINES FROM TERTIARY AMINES USING NON-POLAR HYDROCARBON SOLVENT AND WATER

[75] Inventors: Simon P. Burns, Austin; John M. Walton, Georgetown; Edward E. McEntire, Austin, all of Tex.

[73] Assignee: Texaco Inc., White Plains, N.Y.

[21] Appl. No.: 581,464

[22] Filed: Feb. 17, 1984

[51] Int. Cl.$^4$ .................. C07D 265/30; C07D 265/32; C07D 295/12; C07C 87/00
[52] U.S. Cl. .................................... 544/177; 564/499; 564/437
[58] Field of Search ................. 544/177; 564/499, 437

[56] References Cited

U.S. PATENT DOCUMENTS

| | | | |
|---|---|---|---|
| 3,154,544 | 10/1964 | Langdon et al. | 544/177 X |
| 3,192,208 | 7/1965 | Easton et al. | 544/177 |
| 3,331,756 | 7/1967 | Currier et al. | 544/402 |
| 3,400,129 | 9/1968 | Cour et al. | 544/351 |
| 3,890,315 | 6/1975 | Chen | 544/177 X |
| 4,299,956 | 11/1981 | Brennan | 544/177 |
| 4,299,957 | 11/1981 | Brennan | 544/177 |
| 4,442,306 | 4/1984 | Muller et al. | 564/479 |

FOREIGN PATENT DOCUMENTS

| | | |
|---|---|---|
| 1407305 | 6/1965 | France . |
| 0127349 | 10/1980 | Japan . |
| 2084132 | 4/1982 | United Kingdom . |
| 472122 | 6/1976 | U.S.S.R. . |

OTHER PUBLICATIONS

Ferguson—Textbook of Organic Chemistry, D. Van Nostrand Co. Aug. 1961.
C. A. vol. 70, 1969, 68384d.

Primary Examiner—John E. Kittle
Assistant Examiner—Mukund J. Shah
Attorney, Agent, or Firm—Jack H. Park; Kenneth R. Priem; Richard A. Morgan

[57] ABSTRACT

A method for the separation of primary amines such as bis-(2-aminoethyl)ether from tertiary amines such as N-(2-methoxyethyl)morpholine which have close boiling points via extraction using a non-polar hydrocarbon solvent and water is described. The water may be added to a stream containing both bis-(2-aminoethyl)ether and N-(2-methoxyethyl)morpholine before extraction with the non-polar hydrocarbon is performed. The N-(2-methoxyethyl)morpholine is selectively removed by the hydrocarbon.

11 Claims, No Drawings

METHOD OF SEPARATING PRIMARY AMINES FROM TERTIARY AMINES USING NON-POLAR HYDROCARBON SOLVENT AND WATER

BACKGROUND OF THE INVENTION

Cross-Reference to Related Application

This application is related to U.S. patent application Ser. No. 581,465, filed of even date, which concerns a method of separating primary amine from tertiary amines using a non-polar hydrocarbon alone or in conjunction with a polyhydroxylic compound.

1. Field of the Invention

The invention relates to amine liquid-liquid extration separation methods and more particularly relates to methods for the separation of primary amines from tertiary amines which have close boiling points, by means of a non-polar hydrocarbon solvent and water.

2. Description of Other Relevant Methods in the Field

Bis-(2-aminoethyl)ether (BAEE) and N-(2-methoxyethyl)morpholine (MEM) are co-products in the production of morpholine when diethylene glycol and ammonia are used as the reactor feed. These two co-products are very difficult to separate by conventional distillation because of their close boiling points. It would be advantageous to separate these two compounds because BAEE can be methylated to form β-(N,N-dimethylamino)alkyl ethers which are useful as catalysts in polyurethane isocyanate reactions according to U.S. Pat. No. 3,330,782, incorporated by reference herein.

No method has been found for the separation of these two compounds. However, amines have been separated from other compounds according to some of the following techniques.

For example, U.S. Pat. No. 3,033,864 discloses the purification of pyrazines and piperazines by azeotropic distillation. In that patent, the goal was to remove unreacted alkanolamines by using codistillation agents comprising aliphatic hydrocarbons, aromatic hydrocarbons and nuclear chlorinated aromatic hydrocarbons having normal boiling points between about 130° and 200° C. Representative examples given were octane and higher aliphatic hydrocarbons, petroleum fraction mixtures, ethyl cyclohexane, ethylbenzene, the xylenes, diethylbenzene, ethyl toluene, cumene and chlorobenzene.

A process for recovering piperazine from a mixture with triethylenediamine is described in U.S. Pat. No. 3,105,019. The inventors therein found that aliphatic hydrocarbons and especially saturated aliphatic hydrocarbons would be suitable azeotropic agents for the piperazine-triethylenediamine split if the boiling points were in the range from 110° C. to about 200° C., with particularly good results being obtained if the boiling point is within the range from about 140° C. to about 160° C. Specific compounds mentioned and tried were 3-methylheptane, 2-ethyl hexene, 1,2-dimethyl cyclohexane, meta-xylene, nonane, styrene, mesitylene, kerosene and 1-methyl naphthalene.

A method for recovering the major by-products from piperazine reaction residue is presented in U.S. Pat. No. 3,331,756. It was taught therein that hydrocarbons immiscible with diethylenetriamine and boiling within the range of about 175° to about 250° C. would be suitable entrainers for use in the separation of diethylenetriamine and aminoethylpiperazine. Two azeotropic agents mentioned were tetrapropylene and n-dodecane, with tetrapropylene being preferred because it gave a cleaner separation.

Russian Pat. No. 472,122 teaches that diethylenetriamine and aminoethylpiperazine may be separated from reaction mixtures (especially those from the synthesis of a diamine and piperazine) by means of azeotropic rectification using a hydrocarbon mixture boiling at 160° to 174° C. yielding an azeotrope with DETA. The inventors found that the fractionation is simplier with n-decane than with dodecane or tetrapropylene.

The separation of an alkylene open chain polyamine from a piperazine compound may be accomplished by complexing the polyamine with a salt selected from the group consisting of sulfates and chlorides of copper, nickel, cobalt and zinc, according to the invention disclosed in U.S. Pat. No. 3,038,904. The complex compounds are extracted with substances such as chloroform or are allowed to precipitate out. U.S. Pat. No. 3,400,129 reveals that 2-methyl triethylenediamine can be purified in a process which incorporates a two-solvent extraction step. One of the solvents is water and the other is an organic solvent for pyrazines, such as hexene, octene, nonene, benzene, toluene, xylenes, ethyl benzene, propyl benzene, n-hexane, n-heptane, isooctane, n-nonane, methylnonane, chlorobenzene, chlorotoluenes, diethylether, furan and alkylbenzonitriles. The method includes an azeotropic distillation step where 2-methylpiperazine is distilled and a step where the purified 2-methyl triethylenediamine is recovered.

Further, in Advances in Chemistry Series No. 116: Azeotropic Data III, 1973, L. H. Horsley lists a number of binary azeotropic systems.

SUMMARY OF THE INVENTION

The invention relates to a method for the separation of a primary amine from a tertiary amine, both amines having close boiling points, by extracting a mixture containing both compounds with a non-polar hydrocarbon and water to selectively remove the tertiary amine with the hydrocarbon.

DETAILED DESCRIPTION OF THE PREFERRED EMBODIMENTS

The method of this invention will be effective for any separation of a tertiary amine from a primary amine where the amines have close boiling points. For purposes of this discussion, the amines have close boiling points if the materials boil within 3° C. of each other. Of course, if the boiling points are not very close, the amines may be separated by the simpler process of conventional distillation.

The addition of a non-polar hydrocarbon solvent helps to entrain the tertiary amine. The tertiary amine has all of the nitrogen valences occupied and is, therefore, relatively non-polar as compared with the primary amine which has only one substituent on the nitrogen atom. Two amines which fulfill the requirements set out above are bis-(2-aminoethyl)ether and N-(2-methoxyethyl)morpholine.

Bis-(2-aminoethyl)ether (BAEE) and N-(2-methoxyethyl)morpholine (MEM) are both by-products in the production of morpholine from diethylene glycol and ammonia. This method of producing morpholine is referred to in U.S. Pat. Nos. 2,412,209 and 3,151,112, incorporated by reference herein. However, BAEE and MEM are difficult to separate from each other by conventional distillation.

The method of this invention allows for separating these two co-products so that both may be productively used. The technique involves the addition of water to the co-product stream, then extracting with a relatively non-polar solvent, such as cyclohexane. The MEM is extracted into the relatively non-polar phase, leaving the BAEE in the polar phase. Once the BAEE and the MEM have been isolated into separate phases, each can be recovered individually by conventional distillation.

The non-polar hydrocarbons may be linear or branched, cyclic or containing cyclic moieties. The solvent may be any aliphatic, aromatic or alkaryl hydrocarbon having from 1 to 30 carbon atoms and also similarly sized halocarbons which are unreactive with the amines of the mixture to be separated. Examples of suitable solvents are toluene, chlorobenzene, methane, butane, isopentane, cyclohexane, heptane, dodecane, dodecene, kerosene, mineral oil, etc. and mixtures thereof. The polarity of the solvent used should be equal to or less than that of toluene.

The non-polar and polyhydroxylic solvent of both alternatives should be employed in excess quantities, although economic considerations for this novel extraction process will set an upper limit on the amount of solvents which can be used. Generally, the water content is preferred to be 5 to 85 wt.% based on the total weight of water, primary amine and tertiary amine. In turn, the non-polar hydrocarbon content is preferred to be 10 to 90 wt.% based on the total weight of water, primary amine, tertiary amine and hydrocarbon.

The process may be conducted at or near ambient temperatures, but optimization would probably be accomplished at an elevated temperature. The method would be useful throughout temperature and pressure conditions from the freezing point of the amine mixture to the approximate boiling point of the mixture. These extractive solvents may even be useful above the critical point of the mixture. Selectivity to the separation concentration would be dependent on temperature, but would not vary with the pressure.

The invention will be further illustrated by the following example.

EXAMPLE 1

A countercurrent three-stage laboratory extraction was carried out to illustrate the invention. The water in the amine phase was added to the anhydrous amine before the analysis. The results are shown below.

TABLE I

| Stream | Results of Water/Cyclohexane Extraction | | | | Stream Weight, grams |
|---|---|---|---|---|---|
| | Components, Area % by Gas-Liquid Chromatography | | | | |
| | Water | BAEE | MEM | Cyclohexane | |
| Amine Feed | 26.6 | 45.0 | 8.9 | 0.0 | — |
| Cyclohexane Feed | 0.0 | 0.0 | 0.0 | 99.9 | — |
| Amine Phase (Third Stage) | 32.8 | 47.2 | 0.8 | ~0.1 | 20 |
| Cyclohexane Phase (Third Stage) | 0.0 | None Detected | 4.8 | 93.4 | 41 |

The above example illustrates that MEM and BAEE may be separated by this extraction technique. Although batch mixer-settler apparatus was used in these extractions, continuous equipment may be used also.

EXAMPLE 2

In a separatory funnel were combined 173 g of a stripped co-product stream, 280 g of water and 500 ml of toluene. The stripped co-product stream contained 24% MEM, 67% BAEE, with 2.2% morpholine, 1.5% monoethanolamine, 0.4% ethylene glycol, 3.9% aminoethylmorpholine, 0.4% 2-(2-aminoethoxy)ethanol, with the remainder comprising unknown materials. The contents were shaken to equilibrate following a slow phase separation, and each phase analyzed as above by gas-liquid chromatography.

| Non-polar Phase | | Polar Phase | |
|---|---|---|---|
| Area % MEM | MEM:BAEE | Area % BAEE | BAEE:MEM |
| 4.6 | 66 | 18.2 | 4.6 |

Many modifications may be made in the method of this invention by one skilled in the art without departing from the spirit and scope of the inventive method which is defined only by the appended claims. For example, one might adjust the temperature or find a precise combination of solvents which gives a particularly advantageous result.

We claim:

1. A method for the separation of primary and tertiary amines having close boiling points comprising
    extracting a mixture comprising a primary amine and a tertiary amine having close boiling points with a non-polar hydrocarbon; selected from the group consisting of methane, butane, isopentane, cyclohexane, heptane, dodecane, dodecene, kerosene, mineral oil, toluene, chlorobenzene and mixtures thereof, and water to selectively remove the tertiary amine with the non-polar hydrocarbon.

2. The method of claim 1 in which the water content is 5 to 85 wt.% based on the total weight of water, primary amine and tertiary amine.

3. The method of claim 1 in which the non-polar hydrocarbon content is 10 to 90 wt.% based on the total weight of water, primary amine, tertiary amine and hydrocarbon.

4. The method of claim 1 in which the extraction is carried out at a temperature between about the freezing point and about the boiling point of the amine mixture.

5. A method for the separation of bis-(2-aminoethyl)ether from N-(2-methoxyethyl)morpholine comprising
    extracting a mixture comprising bis-(2-aminoethyl)ether and N-(2-methoxyethyl)morpholine with a non-polar hydrocarbon; selected from the group consisting of methane, butane, isopentane, cyclohexane, heptane, dodecane, dodecene, kerosene, mineral oil, toluene, chlorobenzene and mixtures thereof, and water to selectively remove the N-(2-methoxyethyl)morpholine with the non-polar hydrocarbon.

6. The method of claim 5 in which the water content is 5 to 85 wt.% based on the total weight of water, bis-(2-aminoethyl)ether and N-(2-methoxyethyl)morpholine.

7. The method of claim 5 in which the non-polar hydrocarbon content is 10 to 90 wt.% based on the total weight of water, bis-(2-aminoethyl)ether, N-(2-methoxyethyl)morpholine and hydrocarbon.

8. The method of claim 5 in which the method is carried out at a temperature between about the freezing point and about the boiling point of the amine mixture.

9. A method for the separation of bis-(2-aminoethyl ether from N-(2-methoxyethyl)morpholine comprising a. adding to a mixture containing primarily bis-(2-aminoethyl)ether and N-(2-methoxyethyl)morpholine, water of 5 to 85 wt.% based on the total weight of water, bis-(2-aminoethyl)ether and N-(2-methoxyethyl)morpholine, and b. extracting the mixture with a non-polar hydrocarbon solvent selected from the group consisting of methane, butane, isopentane, cyclohexane, heptane, dodecane, dodecene, kerosene and mineral oil to selectively remove the N-(2-methoxyethyl)morpholine.

10. The method of claim 9 in which the non-polar hydrocarbon content is 10 to 90 wt.% based on the total weight of water, bis-(2-aminoethyl)ether, N-(2-methoxyethyl)morpholine and hydrocarbon.

11. The method of claim 9 in which the method is carried out at a temperature between about the freezing point and about the boiling point of the amine mixture.

* * * * *

UNITED STATES PATENT AND TRADEMARK OFFICE
CERTIFICATE OF CORRECTION

PATENT NO. : 4,552,958

DATED : November 12, 1985

INVENTOR(S) : Simon Pierce Burns, John Monte Walton and Edward Enns McEntire

It is certified that error appears in the above-identified patent and that said Letters Patent is hereby corrected as shown below:

Claim 9, line 1, "bis-(2-aminoethyl" should read

--bis-(2-aminoethyl)--

Signed and Sealed this

Eleventh Day of March 1986

[SEAL]

Attest:

DONALD J. QUIGG

Attesting Officer

Commissioner of Patents and Trademarks